US006624191B2

United States Patent
Legrand

(12) United States Patent
(10) Patent No.: US 6,624,191 B2
(45) Date of Patent: *Sep. 23, 2003

(54) 1-O-ALKYLGLYCEROLS FOR PHARMACEUTICAL OR VETERINARY USE FOR PRESERVING AND/OR IMPROVING SPERM

(75) Inventor: Alain Legrand, Jugon-les-Lacs (FR)

(73) Assignee: Universite de Rennes and ID-MER, Rennes (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,059

(22) PCT Filed: Jun. 27, 1997

(86) PCT No.: PCT/FR97/01160

§ 371 (c)(1), (2), (4) Date: Feb. 11, 1999

(87) PCT Pub. No.: WO98/00120

PCT Pub. Date: Jan. 8, 1998

(65) Prior Publication Data

US 2001/0051164 A1 Dec. 13, 2001

(30) Foreign Application Priority Data

Jun. 28, 1996 (FR) .............................. 96 08314

(51) Int. Cl.$^7$ .............................................. A61K 31/23
(52) U.S. Cl. ...................................................... 514/506
(58) Field of Search ................................. 424/420, 435; 514/506, 715

(56) References Cited

FOREIGN PATENT DOCUMENTS

EP        0 321 428 A     6/1989
EP        0 333 678 A     9/1989
EP        0 335 844 A     10/1989

OTHER PUBLICATIONS

Effects of platelet activating factor on mouse oocyte fertilization in vitro, Am. J. Obstet. Gynecol., Minhas, et al. 1714–1717.

"Enhanced Embryo Development of Rabbit Oocytes Fertilized in Vitro with Platelet Activating Factor (PAF)—Treated Spermatozoa," Journal of Assisted Reproduction and Genetics, vol. 10, No. 1, 1993, Roudebush, et al. 91–94.

"The Involvement of Platelet Activating Factor in Ovulation," Science Jan. 1989, Abisogun, et al. 381–383.

"The comparative estimation of cytotoxicity and cryoprotective efficiency of glycerol and its alkyl ethers upon freezing of human sperm." Chemical Abstracts vol. 110, No. 25. Columbus, Ohio. XP002030147, Jun. 19, 1989.

"Stellenwert der Neutralfette als potentielle Energiequelle der menschlichen Spermatozoen" Nissen, et al., Fette, Seifen, Anstrichmittel, vol. 2, pp. 595, 599. XP002030146, Jan. 28, 1983.

Copy of Search Report for PCT/FR97/01160.

"Biology of Reproduction" *A Publication of the Society for the Study of Reproduction.* Sep. 24, 2001 Figures 96 and 97 of a thesis presented Jun. 2001.

*Primary Examiner*—Gollamudi S. Kishore
(74) *Attorney, Agent, or Firm*—Merchant & Gould P.C.

(57) ABSTRACT

The invention relates to new uses for 1-O-alkylglycerols and notably such of those compounds naturally present in fish liver oils and notably the liver oils of sharks. More precisely, the invention relates to the use of such compounds for the production of medicines for human use to combat sterility, to produce alimentary adjuvants for veterinary use that permit an increase in fertilization yields in animal breeding, to produce sperm storage adjuvants and to produce factors that encourage the mobility of spermatozoons during in vitro fertilization.

21 Claims, No Drawings

1-O-ALKYLGLYCEROLS FOR PHARMACEUTICAL OR VETERINARY USE FOR PRESERVING AND/OR IMPROVING SPERM

The invention relates to both the pharmaceutical and the veterinary fields.

More precisely, the invention relates to reproduction and notably finds application in the field of sterility treatment for human beings and in the field of improving fertility in animals. The invention also finds application in the field of in vitro fertilisation and assisted procreation.

The objective of this invention is to provide new uses for known compounds in which they play a role within the field of reproduction. More precisely, one of the objectives of this invention is to provide a use of such compounds in combating sterility in men.

Another objective of the invention is to describe new uses of such compounds in increasing the fertility of breeding animals and hence in improving the productivity of such animal breeding.

Yet another objective of this invention is to disclose the new use of such compounds to encourage in vitro fertilisation and also to permit improved storage of sperm during the carrying out of methods of assisted procreation.

These various objectives and others that will become apparent in what follows are achieved thanks to the invention which relates to a medicine for human use to combat masculine sterility, characterised in that it comprises at least one 1-O-alkylglycerol compound. According to this invention, in effect it has been discovered that such compounds allow one to increase in a significant way the motor functions of the spermatozoons and hence they can be used to combat certain cases of masculine sterility.

According to a preferred variant, such a medicine is designed to be administered by the oral route in such a way as to have the advantage of being easily absorbed and hence of facilitating the treatment for which it has been prescribed.

The invention also relates to an alimentary adjuvant for veterinary use intended to increase fertilisation yields in animal breeding characterised in that it includes at least one such 1-O-alkylglycerol compound. This new use is also based on the potential of such compounds to encourage the motor functions of the spermatozoons.

The invention also relates to a conservation adjuvant for sperm characterised in that it comprises at least one 1-O-alkylglycerol. Such a compound allows the fertilisation power of the stored sperm to be improved which permits an improvement in the chances of success when carrying out assisted procreation procedures.

Finally, the invention also relates to a factor that encourages the mobility of the spermatozoons during in vitro fertilisation characterised in that it comprises at least one 1-O-alkylglycerol compound. Such a factor is capable of improving the chances of success in the operation of in vitro fertilisation.

Preferably, the 1-O-alkylglycerol compound used for all these new applications is of natural origin. Alkylglycerols are present in small quantities in several natural products. They are found in the haematopoietic organs particularly in the bone marrow and also in relatively large concentration in maternal milk. However it is in certain fish liver oils and in particular in the liver oils of certain species of shark that these etherlipids are to be found in greatest abundance. These oils contain more than 50% alkylglycerols.

This is the reason why the preferred source of the compound being used is fish liver oil and advantageously shark liver oil. The invention therefore provides a path for the economic development of this type of product that stems from the fishing industry and which traditionally is a low cost product.

Preferably said 1-O-alkylglycerol is chosen from the group made up by 18:1 alkyl-1-glycerol, 16:1 alkyl-1-glycerol and 16:0 alkyl-1-glycerol. These three compounds are, in effect, those which are present in the greatest quantities in the shark liver oils. This is particularly so for 18:1 alkyl-1-glycerol.

The activity of the 1-O-alkylglycerols in the context of the uses described above results from the fact that such compounds are the precursors of Platelet Activating Factor (PAF).

Platelet Activating Factor (PAF) is a general term that groups together the derivatives of glycerophosphocholine (GPC). The alkyl-PAF is the most active compound and its general structure is 1-O-alkyl-2-acetyl-sn-glycero-3-phosphocholine. The number of carbon atoms and the degree of unsaturation in the alkyl chain can vary without modifying in any significant way its biological activity. The alkenyl-PAFs or plasmalogenic PAFs (1-O-alk-1'-enyl-2-acetyl-sn-glycero-3-phosphocholine) and the acyl-PAFs (1-acyl-2-acetyl-sn-glycero-3-phosphocholine) are much less powerful than the alkyl-PAFs. PAF has a wide range of biological activity at very low concentrations (from $10^{-10}$ to $10^{-9}$M). Initially identified as a mediator released by the leucocytes and capable of activating the blood platelets, it has been established that PAF plays a role in the field of reproduction. Production of PAF has been shown to occur during ovulation (Abisogun A.O. et al., (1989) Science 243:381–383). It has also been demonstrated that PAF increases the motor function of the spermatozoons of various animal species and of man and that the treatment of the spermatozoons by PAF increases their power of fertilisation of ovocytes of the rabbit and of the mouse (Roudebush et al., (1993) J. Assis. Reprod. Gen. 10:91–94; Brijinder et al., (1989) Am. J. Obstet. Gynecol. 161:1714–1717).

It should be noted however that in these various pieces of work, there has not been any interest taken in the possibility of using the precursors of PAF for uses such as those proposed by the invention.

It should equally be noted that it has already been suggested in the state of the technology that PAF itself be used in order to try to improve the properties of stored sperm. However such a use had ended in failure because of the delicate handling required due to the very high biological activity of this product.

With the aim of confirming the activity of the 1-O-alkylglycerols for the specific applications mentioned above, various tests have been carried out.

A first series of tests has been carried out so as to verify that these compounds are integrated into the spermatozoons.

For this purpose, different samples of human sperm, boar sperm and rabbit sperm were placed under incubation for 24 hours at 35° C., in the presence of an extract from shark liver oil that contained a mixture of 1-O-alkylglycerols labelled with tritium (said samples comprising 54 to 65% of 18:01 alkyl-1-glycerol, 5 to 15% of 16:1 alkyl-1-glycerol and 5 to 10% of 16:0 alkyl-1-glycerol as well as other alkylglycerols in smaller quantities). These tests were carried out using said mixture at a concentration of $10^{-5}$ Mol/l of 1-O-alkylglycerols.

Following this incubation, the lipid fraction of the spermatozoons was extracted and the radioactivity of this fraction was measured. The results show that:

about 12% of the initial radioactivity is found in the total lipids of the boar spermatozoons about 10% of the initial radioactivity is found in the total lipids of the rabbit spermatozoons about 5% of the initial radioactivity is found in the total lipids of the human spermatozoons.

These results demonstrate well the cellular integration of the 1-O-alkylglycerols according to the invention in the spermatozoons.

A more precise study has shown that a small fraction of this radioactivity was incorporated into the phospholipids (phosphatidyl choline and phosphatidyl ethanolamine), namely 0.1% in each of the boar and rabbit classes and less than 1% for man. In the neutral lipids, a very small fraction is metabolised in the form of 1-alkyl-2-3-diacylglycerols (less than 0.1%) for the three species. The remainder of the radioactivity is found in the native form of the 1-O-alkylglycerols.

A second series of tests has been carried out and has allowed one to demonstrate that the mobility of boar spermatozoons was found to have been significantly increased after an incubation of from 24 to 96 hours in the presence of the alkylglycerol mixture mentioned above at the rate of $10^{-5}$ Mol/l of 1-O-alkylglycerols.

What is claimed is:

1. A method of treating masculine sterility by increasing sperm mobility, the method comprising administering at least one 1-O-alkylglycerol compound selected from the group consisting of 16:0 alkyl-1-glycerol, 18:1 alkyl-1-glycerol, 16:1 alkyl-1-glycerol to a mammalian subject.

2. A method according to claim 1, wherein said 1-O-alkylglycerol compound is administered orally.

3. A method of increasing fertilization yields in breeding animals by increasing sperm mobility, the method comprising administering at least one 1-O-alkylglycerol compound selected from the group consisting of 16:0 alkyl-1-glycerol, 18:1 alkyl-1-glycerol, and 16:1 alkyl-1-glycerol as a veterinary alimentary adjuvant to a mammalian subject.

4. A method of storing sperm to preserve their mobility, the method comprising using a storage adjuvant comprising at least one 1-O-alkylglycerol compound selected from the group consisting of 16:0 alkyl-1-glycerol, 18:1 alkyl-1-glycerol, and 16:1 alkyl-1-glycerol, wherein said storage adjuvant is administered to a sperm sample.

5. A method for increasing motor function of spermatozoa during in vitro fertilization comprising administering a factor comprising at least on 1-O-alkylglycerol compound selected from the group consisting of 16:0 alkyl-1-glycerol, 18:1 alkyl-1-glycerol, and 16:1 alkyl-1-glycerol, wherein said factor is administered to a mammalian subject.

6. A method according to claim 1, wherein said 1-O-alkylglycerol compound is of natural origin.

7. A method according to claim 6, wherein said 1-O-alkylglycerol compound comes from fish liver oil.

8. A method according to claim 7, wherein said 1-O-alkylglycerol compound comes from shark liver oil.

9. A method according to claim 3, wherein said 1-O-alkylglycerol compound is of natural origin.

10. A method according to claim 9, wherein said 1-O-alkylglycerol compound comes from fish liver oil.

11. A method according to claim 10, wherein said 1-O-alkylglycerol compound comes from shark liver oil.

12. A method according to claim 4, wherein said 1-O-alkylglycerol compound is of natural origin.

13. A method according to claim 12, wherein said 1-O-alkylglycerol compound comes from fish liver oil.

14. A method according to claim 13, wherein said 1-O-alkylglycerol compound comes from shark liver oil.

15. A method for increasing motor function of spermatozoa according to claim 5, wherein said 1-O-alkylglycerol compound is of natural origin.

16. A method for increasing motor function of spermatozoa according to claim 15, wherein said 1-O-alkylglycerol compound comes from fish liver oil.

17. A method for increasing motor function of spermatozoa according to claim 16, wherein said 1-O-alkylglycerol compound comes from shark liver oil.

18. A method of treating masculine sterility by increasing sperm mobility, the method comprising administering a composition in an effective amount, wherein said composition comprises at least one 1-O-alkylglycerol compound selected from the group consisting of: 16:0 alkyl-1-glycerol, 18:1 alkyl-1-glycerol, and 16:1 alkyl-1-glycerol, wherein said 1-O-alkylglycerol compound is derived from fish liver oil to a patient in need thereof.

19. A method of increasing fertilization yields in breeding animals by increasing sperm mobility, the method comprising administering a composition in an effective amount wherein said composition comprises at least one 1-O-alkylglycerol compound selected from the group consisting of: 16:0 alkyl-1-glycerol, 18:1 alkyl-1-glycerol, and 16:1 alkyl-1-glycerol, wherein said 1-O-alkylglycerol compound is derived from fish liver oil to an animal in need thereof.

20. A method of preserving the motor function of spermatozoa during the storage and conservation thereof, the method comprising contacting sperm with a composition wherein said composition comprises at least one 1-O-alkylglycerol compound selected from the group consisting of: 16:0 alkyl-1-glycerol, 18:1 alkyl-1-glycerol, and 16:1 alkyl-1-glycerol, wherein said 1-O-alkylglycerol compound is derived from fish liver oil.

21. A method of preserving the motor function of spermatozoa during in vitro fertilization comprising contacting spermatozoa with a composition wherein said composition comprises at least one 1-O-alkylglycerol compound selected from the group consisting of: 16:0 alkyl-1-glycerol, 18:1 alkyl-1-glycerol, and 16:1 alkyl-1-glycerol, wherein said 1-O-alkylglycerol compound is derived from fish liver oil.

* * * * *